(12) United States Patent
Fecant

(10) Patent No.: US 8,841,231 B2
(45) Date of Patent: Sep. 23, 2014

(54) PROCESS FOR THE PREPARATION OF PALLADIUM-BASED CATALYSTS AND USE OF SAID CATALYSTS IN SELECTIVE HYDROGENATION

(75) Inventor: Antoine Fecant, Brignais (FR)

(73) Assignee: IFP Energies Nouvelles, Rueil Malmaison, Cedex (FR)

( * ) Notice: Subject to any disclaimer, the term of this patent is extended or adjusted under 35 U.S.C. 154(b) by 156 days.

(21) Appl. No.: 13/324,067

(22) Filed: Dec. 13, 2011

(65) Prior Publication Data

US 2012/0149955 A1 Jun. 14, 2012

(30) Foreign Application Priority Data

Dec. 14, 2010 (FR) ...................... 10 04878

(51) Int. Cl.
| | |
|---|---|
| C07C 5/11 | (2006.01) |
| B01J 37/08 | (2006.01) |
| B01J 23/00 | (2006.01) |
| B01J 35/02 | (2006.01) |
| B01J 37/02 | (2006.01) |
| B01J 37/16 | (2006.01) |
| B82Y 40/00 | (2011.01) |
| B82Y 30/00 | (2011.01) |
| C10G 45/46 | (2006.01) |
| B01J 23/44 | (2006.01) |
| C07C 5/05 | (2006.01) |
| C10G 45/34 | (2006.01) |

(52) U.S. Cl.
CPC ................ B01J 23/44 (2013.01); C10G 45/46 (2013.01); B01J 37/0203 (2013.01); B01J 37/0221 (2013.01); C07C 2523/44 (2013.01); C10G 2300/202 (2013.01); C10G 2300/1096 (2013.01); C07C 5/05 (2013.01); B01J 37/0219 (2013.01); C10G 2300/1088 (2013.01); B01J 37/0211 (2013.01); C10G 45/34 (2013.01); Y10S 977/84 (2013.01); Y10S 977/902 (2013.01)
USPC ........... 502/300; 585/269; 502/325; 977/840; 977/902

(58) Field of Classification Search
None
See application file for complete search history.

(56) References Cited

U.S. PATENT DOCUMENTS

| | | |
|---|---|---|
| 4,361,500 A | 11/1982 | Mathe et al. |
| 2002/0132042 A1 | 9/2002 | Merricks et al. |
| 2002/0151433 A1 | 10/2002 | Yoshihara et al. |
| 2008/0039536 A1 | 2/2008 | Fisher et al. |
| 2010/0075841 A1 | 3/2010 | Chiba et al. |

FOREIGN PATENT DOCUMENTS

| | | |
|---|---|---|
| EP | 1 201 787 A2 | 5/2002 |
| EP | 1 247 574 A1 | 10/2002 |
| EP | 2 075 061 A1 | 7/2009 |
| GB | 2 052 294 A | 1/1981 |
| JP | 2002-1119 A | 1/2002 |
| JP | 2005-314739 A | 11/2005 |
| WO | WO 2005/123255 A1 | 12/2005 |

OTHER PUBLICATIONS

Search Report of FR 1004878 (Sep. 23, 2011).

*Primary Examiner* — Melvin C Mayes
*Assistant Examiner* — Douglas Call
(74) *Attorney, Agent, or Firm* — Millen, White, Zelano & Branigan, P.C.

(57) ABSTRACT

The invention concerns a novel process for the preparation of supported metallic catalysts in which the metallic phase is deposited in the form of agglomerates of nanoparticles of metallic oxide and forms a layer of fine thickness at the surface of the support. The process for the preparation of a catalyst comprises preparing in aqueous phase a colloidal suspension of agglomerates of nanoparticles of metallic oxide, then depositing that suspension on a porous support, drying the catalyst precursor obtained, and optionally calcining and reducing the precursor by means of any reducing compound. The invention also concerns the catalysts obtained by said process and their uses in reactions for the transformation of unsaturated organic compounds. The invention is applied to the refining field and more particularly to the treatment of gasolines obtained by steam cracking and/or obtained by catalytic cracking.

18 Claims, No Drawings

PROCESS FOR THE PREPARATION OF PALLADIUM-BASED CATALYSTS AND USE OF SAID CATALYSTS IN SELECTIVE HYDROGENATION

The invention concerns a novel process for the preparation of supported metallic catalysts in which the metallic phase is deposited in the form of agglomerates of nanoparticles of metallic oxide and forms a layer of fine thickness at the surface of the support. It also concerns the catalysts obtained by the process and their uses in reactions for the transformation of unsaturated organic compounds. The invention is applied to the refining field and more particularly to the treatment of gasolines obtained by steam cracking (dripolene) and/or obtained by catalytic cracking.

Monounsaturated organic compounds such as for example ethylene and propylene are at the origin of the production of polymers, plastic materials and other chemical products involving added value. Those compounds are obtained from natural gas, naphtha or diesel which are treated by steam cracking or catalytic cracking processes. Those processes are operated at high temperature and, in addition to the desired monounsaturated compounds, produce polyunsaturated organic compounds such as acetylene, propadiene and methylacetylene (or propyne), buta-1,2-diene and buta-1,3-diene, vinylacetylene and ethylacetylene and other polyunsaturated compounds whose boiling point corresponds to the $C5^+$ gasoline fraction (gasolines containing hydrocarbon compounds having more than 5 carbon atoms). Those polyunsaturated compounds are highly reactive and lead to parasitic reactions in polymerisation units. It is therefore necessary to remove them before usefully employing the cuts containing monounsaturated organic compounds.

Thus for example the steam-cracking C2 cut (gasoline containing hydrocarbon compounds having 2 carbon atoms) can be of the following mean composition by volume: 1.2% by weight of acetylene, 83.5% by weight of ethylene and 15.3% by weight of ethane. That cut can be used in a polymerisation unit if it complies with the specifications concerning the levels of concentration of acetylene for polymerisation units, that is to say if the acetylene concentration is lower than 2 ppm by weight (ppm:parts per million). It is the same for the C3 and C4 cuts or the other cuts in respect of which the specifications are also very severe for uses thereof in polymerisation units.

Selective hydrogenation is the main treatment developed for specifically removing undesirable polyunsaturated compounds from dripolenes or from catalytic cracking gasolines primarily containing monoolefins. It permits the conversion of the polyunsaturated compounds towards the corresponding alkenes or aromatics while avoiding total saturation thereof and therefore the formation of the corresponding alkanes. Thus in a C2 cut, after a selective hydrogenation treatment, the acetylene content will be reduced while the ethylene content will be increased and the ethane content remains practically unchanged.

Selective hydrogenation catalysts are generally based on metals of group VIII of the periodic table of elements, preferably palladium or nickel. The active phase of the catalysts is in the form of small metallic particles deposited on a support which can be a refractory oxide in the form of balls, extrudates, trilobes or forms involving other geometries. The proportion of metal, the size of the particles of metal and the distribution of the active phase in the support are some of the criteria which have importance in terms of activity and selectivity of those catalysts.

The supported metallic particles can be of a mean size of between 1 and 5 nm. That size is matched to the requirements of the selective hydrogenation reactions. In fact the speed of reaction for the hydrogenation of polyunsaturated molecules such as diolefins or acetylenics depends on the size of the metallic particles. That result is generally described by the expression "sensitivity to structure". An optimum is generally observed for a size of the order of 3 to 4 nm, which value can vary in dependence in particular on the molecular mass of the reactants (M. Boudart, W. C. Cheng, J. Catal. 106, 1987, 134, S. Hub, L. Hilaire, R. Touroude, Appl. Catal. 36 1992, 307).

The distribution of the active phase within the selective hydrogenation catalysts plays a decisive part as regards their activity and selectivity. Impregnation of a solution of ionic palladium precursors on a support of refractory oxide type provides that the active species diffuse to the heart of the support. That distribution of the metallic phase in the heart of the support is prejudicial, particularly in the case of reactions controlled by diffusion of the reactants, as is the case with selective hydrogenation. That implies a low level of activity and a low level of selectivity of the catalysts since undesirable secondary reactions then take place. For a hydrogenation catalyst to have good catalytic properties it is preferable for the metallic particles to be deposited at the surface of the support in the form of a layer of small thickness. When the particles are distributed in that way, that is referred to as crust deposit and/or shell catalyst. The finer the thickness of that layer, the more the problems of transfer of intragranular material which can lead to activity defects and a loss of selectivity are avoided.

The use of colloidal solutions of metallic particles or particles of metallic oxide makes it possible to produce catalysts whose size and metallic particle distribution correspond in part to the aforementioned criteria. Patent application EP0979673 describes the preparation of a selective hydrogenation catalyst by impregnation of a colloidal suspension of metallic oxide in aqueous phase on a support.

The use of colloidal solutions of metallic nanoparticles or nanoparticles of metallic oxide in processes for the production of supported catalysts has undergone development in recent years. However that procedure suffers from many disadvantages. In fact the colloidal solutions are not thermally stable. The nanoparticles have a tendency to coalesce and agglomerate causing their precipitation in solution. That aggregation effect normally involves a loss of activity of the nanoparticles. Stabilisation of the nanoparticles and therefore maintaining their character of being finely dispersed in a solution is a fundamental step in synthesis thereof and in deposit thereof on the support. Stabilisation of the nanoparticles is achieved by using stabilising agents. Those agents make it possible to control the size of the nanoparticles upon growth thereof. They make it possible to obtain nanoparticles which are dispersed in a solution and which are of a homogenous size. They thus prevent them from aggregating and precipitating in aqueous solution. The use of such stabilising agents is described in the following documents. Patent application WO 00/29332 describes a process for obtaining a stable colloidal solution of nanoparticles of metallic oxide of a size of 0.5 to 5 nm. The work by Klasovsky et al. (Topic in Catalysis, vol 52, pages 412-423, 2009) studies the preparation of palladium-based selective hydrogenation catalysts by impregnation of a colloidal solution of nanoparticles of palladium oxide which is stabilised by means of a polymer (polyvinylpyrrolidone—PVP) resulting from hydrolysis of $H_2PdCl_4$ in solution with different organic or mineral bases. Finally it is also known from EP0653243 to prepare a transition metal-based catalyst by dissolving a precursor of that metal in solution to which there is added an organic polymer permitting selective distribution of the metallic phase in the macropores of the solid after the catalyst has been shaped. In the above-described processes the metallic nanoparticles which have been stabilised and dispersed in solution in the presence of stabilising agents are then reduced by a reducing agent before being deposited on the support.

In a totally surprising fashion and contrary to the prior-art processes the applicant has found that supported catalysts can be prepared from nanoparticles of metallic oxide which form agglomerates in the presence of at least one agglomerating agent. The invention enjoys the following advantages:

preparation of the supported catalysts with a colloidal solution of agglomerates of nanoparticles of metallic oxide is simplified as it makes it possible to overcome the problem of stability of the nanoparticles, the catalysts obtained in accordance with the process of the invention have a metallic phase which is concentrated at the surface of the support. That gives catalysts having an active phase which is deposited in the form of a crust, the catalysts obtained according to the process of the invention having improved catalytic properties in comparison with the known catalysts.

Hereinafter the groups of chemical elements are specified in accordance with the CAS classification (CRC Handbook of Chemistry and Physics, editor CRC press, editor-in-chief D. R. Lide, 81st edition, 2000-2001). For example group VIII in accordance with the CAS classification corresponds to the metals of columns 8, 9 and 10 in accordance with the new IUPAC classification.

The expressions "nanoparticles of metallic oxide" or "nanoparticles of metal oxide" or "nanoparticles" are used in accordance with the present invention to denote polycrystalline particles of a metal oxide. The size of a nanoparticle is between 1 and 10 nm. Preferably the size of a nanoparticle is between 1 and 5 nm.

The expression "agglomerate" is used in accordance with the present invention to denote an assembly of nanoparticles of metal oxide which combine together under the effect of weak interactions of Van der Waals type or electrostatic interactions to form an agglomerate or an aggregate. The nanoparticles forming the agglomerates are not bonded together chemically by covalent bonds. The size of the agglomerates is between 20 and 200 nm, preferably between 20 and 15 nm, still more preferably between 20 and 100 nm.

The expressions "colloidal aqueous suspension" or "aqueous colloidal suspension" are used in accordance with the present invention to denote an aqueous solution containing nanoparticles of metallic oxide and/or agglomerates of nanoparticles of metallic oxide which are in suspension in the aqueous solution and which form a homogenous mixture without precipitating or sedimenting.

The expression "HSV" is used in accordance with the present invention to denote the hourly space velocity defined as the ratio between the volume flow of the charge to be treated and the volume of catalysts loaded in the reactor. The hourly space velocity is expressed in $h^{-1}$.

The expression "zero charge point" is used in accordance with the present invention to denote the pH of the aqueous solution in which the solid exists at a neutral electrical potential.

A first subject of the invention concerns a process for the preparation of a catalyst in which a colloidal suspension of agglomerates of nanoparticles of metallic oxide is prepared in aqueous phase, then that suspension is deposited a porous support, the resulting catalyst precursor is dried and possibly the precursor is calcined and reduced by means of any reducing compound. In the preparation process according to the invention the colloidal suspension of agglomerates of nanoparticles of metal oxide is prepared in aqueous solution, in the absence of a reducing agent and in the absence of an organic solvent. The step of reducing the metallic oxide to metal is effected after deposit of the colloidal suspension of agglomerates on the support.

Contrary to the prior-art procedures in which the attempt is made to deposit the active phase in the form of nanoparticles which are stabilised and dispersed in solution, the applicant has found that the metallic phase can be deposited on a porous support in a form of agglomerates of nanoparticles of metallic oxide. Surprisingly the deposit of the metallic phase in the form of agglomerates improves the catalytic performances of the catalyst. The use of such agglomerates makes it possible to deposit the metallic phase of the catalyst at the surface of the support in the form of a very thin layer. By virtue of the size of the agglomerates of nanoparticles of metallic oxide they find their diffusion to the heart of the support greatly limited. They therefore remain at the surface of the support and form a thin layer of active phase at its surface. The thickness of the layer will depend on the amount of metals present on the catalyst. Deposit of the metallic phase in the form of agglomerates of nanoparticles of metallic oxide makes it possible to concentrate the nanoparticles at the surface of the catalyst. When the metal is palladium at least 80% of the supported palladium is contained in the interior of a surface layer, the thickness of which does not exceed 80 μm.

The process for the preparation of a catalyst according to the invention comprises a plurality of steps:

(a) a colloidal aqueous suspension of agglomerates of nanoparticles of metallic oxide is prepared, (b) said colloidal aqueous suspension of agglomerates obtained in step (a) is deposited on a porous support, (c) the product obtained in (b) is dried, followed optionally by at least one of the following steps:

(d) the product obtained in step (c) is calcined, and (e) the product obtained in step (c) or step (d) is reduced.

The colloidal suspension of agglomerates of nanoparticles of metallic oxide is obtained by hydrolysis in aqueous solution of at least one salt of a metallic precursor of the metallic oxide in the presence of at least one agglomerating agent. Hydrolysis of the salt of a metallic precursor in acid pH or basic pH results in the formation of nanoparticles of metallic oxide or metallic hydroxide in suspension. In the presence of the agglomerating agent the nanoparticles of metallic oxide combine together without precipitating and form agglomerates, the size of which is between 20 and 200 nm.

In a preferred variant of the process hydrolysis can be effected for example by neutralisation with at least one inorganic base such as ammonia or hydroxides of alkali metals. Preferably the inorganic base is selected from the group formed by ammonia, sodium hydroxide and potassium hydroxide.

When hydrolysis is effected in an acid pH and by neutralisation with an inorganic base the solution of inorganic base is poured into the solution of metal precursor salt.

When hydrolysis is effected in a basic pH and by neutralisation with an inorganic base the solution of metallic precursor salt is poured into the solution of the inorganic base.

The metal of the salt of the metallic precursor is a metal from group VIII. Preferably the metal from group VIII is selected from the group formed by palladium, platinum, cobalt and nickel. Still more preferably the metal is selected from the group formed by nickel and palladium. Very preferably the metal is palladium.

The salt of the precursor of the metal from group VIII can be a salt of a precursor of the metal in question having a degree of oxidation of the metal of higher than 0 and soluble in aqueous solution. The salt of the precursor of the metal of group VIII can be selected from the group formed by a halide, an oxide, a hydroxide, a nitrate or a sulphate of the metal.

More preferably the salt of the metallic precursor can be selected from the group formed by palladium chloride, palladium bromide, palladium iodide, potassium hexachloropalladate, potassium tetrabromopalladate, potassium tetrachloropalladate, sodium hexachloropalladate, sodium tetrachloropalladate, palladium nitrate, palladium sulphate, palladium acetate, platinum chloride, platinum bromide, platinum iodide, potassium hexachloroplatinate, potassium tetrabromoplatinate, potassium tetrachloroplatinate, sodium hexachloroplatinate, sodium tetrachloroplatinate, platinum nitrate, platinum sulphate, platinum acetate, nickel chloride, nickel bromide, nickel iodide, nickel nitrate, nickel sulphate, nickel acetate, cobalt chloride, cobalt bromide, cobalt iodide, cobalt nitrate, cobalt sulphate and cobalt acetate.

Very preferably the palladium precursor salt is selected from the group formed by palladium chloride, palladium nitrate and palladium sulphate. Very preferably the palladium precursor salt is palladium nitrate.

Very preferably the nickel precursor salt is selected from the group formed by nickel chloride, nickel nitrate and nickel sulphate.

The concentration of the aqueous solution of the salt of the precursor of the metal of group VIII is adjusted in accordance with the desired mass proportion of metal to the catalyst. The mass proportion of metal of group VIII in relation to the mass of the support is between 0.01 and 20% by weight, preferably between 0.05 and 10% by weight.

When the metal of group VIII is palladium, the concentration of the aqueous solution of the palladium precursor salt is adjusted in accordance with the desired mass proportion of palladium to the catalyst. The mass proportion of palladium with respect to the mass of the support is between 0.01 and 2% by weight, preferably between 0.05 and 1% by weight.

When the metal of group VIII is nickel, the concentration of the aqueous solution of the palladium precursor salt is adjusted in accordance with the desired mass proportion of nickel to the catalyst. The mass proportion of palladium with respect to the mass of the support is between 1 and 20% by weight, preferably between 2 and 15% by weight.

The agglomerating agent is an organic compound of the formula $(R)_n$—X, with
 n an integer equal to 1 or 4,
 X an ionic group, and
 R a hydrophobic group which can be identical or different when n is equal to 4.

The ionic group X can be an anion or a cation. The hydrophobic group R is formed by a hydrocarbon chain comprising between 2 and 20 carbon atoms. The carbon chain can be straight and/or branched and/or can comprise at least one aromatic. The agglomerating agent may be a cationic or an anionic surfactant.

In aqueous solution the surface of the nanoparticles of metallic oxide is electrically charged. The electrical charge of the surface of those nanoparticles depends on the pH of the aqueous solution and the zero charge point of the metallic oxide. When the pH of the aqueous solution is higher than the zero charge point of the metallic oxide the surface of the nanoparticles is negatively charged. On the other hand when the pH of the aqueous solution is lower than the zero charge point of the metallic oxide the surface of the nanoparticles is positively charged. The agglomerating agent is selected in dependence on the pH of the colloidal aqueous solution. It is of an electrical charge opposite to the surface charge of the nanoparticles. Thus when the pH of the colloidal solution is higher than the zero charge point of the metallic oxide the selected agglomerating agent is positively charged. Mention will be made hereinafter in the specification to cationic agglomerating agent or anionic agglomerating agent. A plurality of molecules of agglomerating agent create electrostatic bonds with the charges of the surface of the nanoparticles which are of opposite electrical sign. The agglomerating agent molecules replace the counter-ions which stabilise the nanoparticles in solution. The hydrophoby of the group R of the agglomerating agent causes the agglomerating agent molecules to combine together and therefore causes the nanoparticles trapped by the agglomerating agent to combine together. Agglomerates of nanoparticles of metallic oxide of a size of between 20 and 200 nm are thus formed.

The addition of agglomerating agent can be effected at the same time as dissolution of the salt of the metallic precursor or after the salt is completely dissolved. It can also be added to the solution containing the inorganic base.

The agglomerating agent is selected in dependence on the pH of the colloidal aqueous solution and in dependence on the zero charge point of the metallic oxide.

When the pH of the colloidal aqueous solution is higher than the zero charge point of the metal oxide the agglomerating agent is a cationic agglomerating agent of the formula $(R)_n$—X wherein:
 X a cation,
 n is equal to 4, and
 R is a straight-chain or branched alkyl comprising 2 to 5 carbon atoms.

The groups R can be identical or different from each other. Preferably the groups R are all identical.

Preferably X is selected from the group formed by the phosphonium function or the ammonium function and very preferably the ammonium function.

Preferably R is selected from the group formed by ethyl, n-propyl, isopropyl, n-butyl, isobutyl, sec-butyl, tert-butyl, n-pentyl, isopentyl, sec-pentyl and tert-pentyl. Preferably R is a straight-chain alkyl comprising 2 to 5 carbon atoms.

Preferably the cationic agglomerating agent is selected from the group formed by tetraethylammonium, tetrapropylammonium, tetrabutylammonium, tetrapentylammonium, tetraethylphosphonium, tetrapropylphosphonium, tetrabutylphosphonium and tetrapentylphosphonium.

The cationic agglomerating agent is added to the metallic precursor solution in the form of a salt in which the counter-ion is a hydroxide.

When the colloidal solution is obtained in accordance with the variant of the process, in which hydrolysis of the salt of the metallic precursor is implemented by neutralisation with an inorganic base, then the cationic agglomerating agent is added in the form of a salt in which the counter-ion is the same as that of the inorganic base used or a counter-ion different from that of the base. The counter-ion of the agglomerating agent is selected from the group formed by hydroxide, bromide, chloride, fluoride, iodide, hydrogen sulphate, tetrafluoroborate and acetate. Preferably the counter-ion is a hydroxide. Very preferably the cationic agglomerating agent is selected from the group formed by tetrabutylammonium hydroxide, tetrapropylammonium hydroxide and tetraethylammonium hydroxide.

When the pH of the colloidal solution is lower than the zero charge point of the metal oxide the agglomerating agent is an anionic agglomerating agent of the formula $(R)_n$—X wherein:

X is an anion, n is equal to 1, and

R is a group of the formula $(B)_p\text{-}(A)_m\rightarrow$ wherein m is an integer equal to 0 or 1, p is an integer equal to 0 or 1, A is a substituted or unsubstituted aromatic, B is straight-chain or branched hydrocarbon chain comprising between 5 and 14 carbon atoms, $\rightarrow$ symbolises attachment of the group R to X by a covalent bond.

Preferably A is selected from the group formed by phenyl, methylphenyl and dimethylphenyl.

When p=0 and m=1 then A is selected from the group formed by methylphenyl, dimethylphenyl and phenyl.

When p=1 and m=0 then B is a branched or straight chain comprising between 5 and 12 carbon atoms.

When p=1 and m=1 then A is a phenyl and B is a branched or straight chain comprising between 5 and 12 carbon atoms.

Preferably the anion is a carboxylate function or a sulphonate function.

The anionic agglomerating agent is added to the metallic precursor solution in the form of a salt in which the counter-ion is sodium. Preferably the anionic agglomerating agent in salt form can be selected from the group formed by sodium dodecyl sulphate, sodium dodecane sulphonate, sodium dodecylbenzene sulphonate, sodium benzene sulphonate, sodium toluene sulphonate, sodium xylene sulphonate, sodium octanoate, sodium nonanoate, sodium decanoate, sodium undecanoate, sodium dodecanoate and sodium tridecanoate. Very preferably the anionic agglomerating agent is selected from the group formed by sodium dodecyl sulphate and sodium dodecylbenzene sulphonate.

When the colloidal solution is obtained in accordance with the variant of the process, in which hydrolysis of the metallic precursor salt is effected by neutralisation with an inorganic base then the anionic agglomerating agent is added in the form of a salt in which the counter-ion is the same as that of the inorganic base used or a counter-ion different from that of the base. The counter-ion of the anionic agglomerating agent is selected from the group formed by lithium, sodium and potassium. Preferably the counter-ion is sodium. Preferably the anionic agglomerating agent in salt form can be selected from the group formed by sodium dodecyl sulphate, lithium dodecyl sulphate, sodium dodecane sulphonate, sodium dodecylbenzene sulphonate, sodium benzene sulphonate, sodium toluene sulphonate, sodium xylene sulphonate, sodium octanoate, sodium nonanoate, sodium decanoate, sodium undecanoate, sodium dodecanoate and sodium tridecanoate. Very preferably the anionic agglomerating agent is selected from the group formed by sodium dodecyl sulphate and sodium dodecylbenzene sulphonate.

The anionic or cationic agglomerating agent can be synthesised by any organic synthesis procedures well known to the man skilled in the art.

The molar ratio between the anionic or cationic agglomerating agent and the salt of the metallic precursor is between 0.001 and 100, preferably between 0.01 and 50, very preferably between 0.02 and 10.

Preparation of said colloidal suspension is effected at a temperature between 10° and 50° C., preferably between 15° and 30° C. and under normal pressure conditions (atmospheric pressure).

The colloidal suspension of agglomerates, that is prepared in that way, is such that at least 20% by number of the nanoparticles of metal oxide are in the form of agglomerates of a size of 10 to 200 nm, preferably at least 30% by number of the nanoparticles of metal oxide are in the form of agglomerates of a size of 10 to 200 nm and very preferably at least 50% by number of the nanoparticles of metal oxide are in the form of agglomerates of a size of 10 to 200 nm. Preferably the colloidal suspension of agglomerate, that is prepared in that way, is such that between 20% and 95% by number of the nanoparticles of metal oxide are in the form of agglomerates, preferably between 30% and 90% by number of the nanoparticles of metal oxide are in the form of agglomerates and very preferably between 50% and 90% by number of the nanoparticles of metal oxide are in the form of agglomerates.

The size of the agglomerates can be measured by transmission electron microscopy (TEM). The distribution by number of the nanoparticles of metal oxide in the form of agglomerates and in the form of isolated particles is obtained by a counting operation on the TEM images. The counting operation is effected on the basis of a substantial number of images to count 200 to 1000 particles. The assembly of images is then processed to count off particles present in the form of agglomerates and isolated particles. The ratio between those two values gives the proportion by number of nanoparticles of metal oxide in the form of agglomerates.

The colloidal suspension of agglomerates is deposited on a porous support. Deposit of that suspension can be effected using all procedures known to the man skilled in the art. Impregnation of the support can be effected by dry impregnation, in excess or in insufficiency, in a static or dynamic mode. Dry impregnation is preferred. Impregnation can be effected in one or more successive impregnation operations.

Impregnation is preferably effected under conditions in which the volume of solution approximately corresponds to the porous volume of the support. Preferably the colloidal suspension of agglomerates is poured onto the porous support. That procedure can be effected either discontinuously, that is to say the step of preparing the colloidal suspension precedes the step of impregnation on the support and the essential part of the colloidal suspension is sent in a single operation towards the impregnation step, or continuously, that is to say the product obtained in the first step is then passed immediately to the second step.

The support can comprise at least one refractory oxide selected from the group formed by oxides of magnesium, aluminium, silicon, zirconium, thorium, or titanium, alone or in mixture with each other or with other oxides of the periodic table such as silica-alumina. Preferably the support is an aluminium oxide (alumina) or silica. The support can also be a carbon, a silico-aluminate, a clay or any other compound known for being used as a support. Preferably the support has a BET surface area of between 5 and 300 m$^2$/g, still more advantageously between 10 and 200 m$^2$/g. The BET specific surface area is measured by physisorption with nitrogen. The total porous volume of the support is generally between 0.1 and 1.5 cm$^3$/g. The total porous volume is measured by mercury porosimetry in accordance with the standard ASTM D4284-92 with a wetting angle of 140°, for example by means of an apparatus model Autopore III of the brand Micromeritics.

The support can be put in the form of balls, extrudates, trilobes, pellets or agglomerates which are irregular and non-spherical, the specific shape of which can result from a crushing step or monolith. Advantageously the support is in the form of balls or extrudates.

The impregnated catalyst is then dried to remove all or a part of the water introduced in the impregnation operation, preferably at a temperature of between 50 and 250° C., more preferably between 70° C. and 200° C. Drying is effected in air or in an inert atmosphere (for example nitrogen).

Possibly the dried catalyst is washed at a temperature of between 5° C. and 100° C., preferably between 15° C. and 50° C., and preferably the liquid used for that washing step is water or ethanol. A second drying step is then effected as described hereinbefore.

The catalyst is then calcined in a gas flow, preferably with air, hydrogen, nitrogen or a mixture of at least two of those gases at a HSV between 100 and 5000 $h^{-1}$. The calcination temperature is generally between 150° C. and 900° C., preferably between about 200° C. and about 500° C. The calcination time is generally between 0.5 hour and 24 hours, preferably between 1 hour and 12 hours. The calcination step can be carried out using rising temperature stages, until the defined maximum target temperature is reached.

The catalyst is generally reduced. That step is preferably carried out in the presence of a reducing gas in situ, that is to say in the reactor in which catalytic transformation is performed, comprising between 25 vol % and 100 vol % of hydrogen, preferably 100 vol % of hydrogen. In that case the reducing gas is hydrogen. Preferably that step is carried out at a temperature of between 50° C. and 400° C., still more preferably between 80° C. and 160° C.

At the end of the catalyst preparation steps the content by mass of metal of group VIII with respect to the mass of the support is between 0.01 and 20% by weight, preferably between 0.05 and 10% by weight. When the metal of group VIII is palladium the proportion by mass of palladium with respect to the mass of support is between 0.01 and 2% by weight, preferably between 0.05 and 1% by weight.

In accordance with a variant for preparation of the catalyst it is prepared in a number of impregnation operations. For the catalysts prepared in two impregnation operations the sequences can be as follows:

impregnation No 1—drying—impregnation No 2—drying—calcination.
impregnation No 1—drying—calcination—impregnation No 2—drying—calcination.

The invention also concerns the catalyst obtained from the above-described preparation process.

Another subject of the invention is use of the catalyst obtained by the process described hereinbefore in a reaction for transformation of organic compounds. Thus the catalyst obtained with the process of the invention can be used in reactions involving cuts or formations of carbon-carbon bonds. The catalyst obtained with the process of the invention permits selective hydrogenation of the compounds comprising acetylenic, dienic, olefinic, aromatic, ketone, aldehyde, acid and/or nitro functions. The catalyst obtained with the process of the invention can also be used for hydrogenation of carbon monoxide to methanol or alcohol with C1-C6 after an increase in the alkyl chain. It can also be used for the formation of dimethylether by condensation of two molecules of methanol. Finally the catalyst obtained with the process of the invention can also be used for reactions for isomerisation or hydroisomerisation, and hydrogenolysis of hydrocarbon compounds. Preferably the catalyst obtained with the process of the invention can be used for a reaction for the selective hydrogenation of compounds comprising at least one dienic and/or acetylenic function.

The operating conditions used for those reactions are as follows: a temperature of between 0 and 500° C., preferably between 25 and 350° C., a pressure of between 0.1 and 20 MPa, preferably between 0.1 and 10 MPa, an hourly space velocity (HSV) of between 0.1 and 50 $h^{-1}$, preferably between 0.5 and 30 $h^{-1}$ for a liquid charge; and between 500 and 30,000 $h^{-1}$, preferably between 500 and 15,000 $h^{-1}$ for a gaseous charge. When hydrogen is present the ratio by volume of hydrogen to the charge is between 1 and 500 liters per liter, preferably between 10 and 250 liters per liter.

Use of the catalyst prepared in accordance with the process of the invention and the conditions of use thereof are to be adapted by the user to the reaction and the technology used. Generally implementation is effected by injection of the hydrocarbon charge to be treated and hydrogen into at least one reactor containing the catalyst, the reactor being a fixed bed, moving bed or boiling bed reactor, preferably a fixed bed reactor. All of the charge is preferably injected at the intake of the reactor where the selective hydrogenation reaction takes place. However it may be advantageous in certain cases to inject a fraction or all of the charge between two consecutive catalytic beds in the reactor. That method of implementation makes it possible in particular to continue to keep the reactor operational even when the intake of the reactor is blocked with deposits of polymers, particles or gums present in the charge.

The selective hydrogenation process comprises bringing a hydrocarbon charge comprising at least one polyunsaturated compound into contact with the catalyst obtained with the above-described process.

The hydrocarbon charge comprises at least one polyunsaturated compound and is selected from the group formed by the cuts resulting from catalytic cracking, steam cracking C2 cuts, steam cracking C3 cuts, steam cracking C4 cuts, steam cracking C5 cuts and steam cracking gasolines also referred to as dripolenes. The steam cracking C5 cuts and the dripolenes are referred to hereinafter in this description as a C5* cut.

Selective hydrogenation of the C2, C3, C4 and C5* cuts can be effected in gas or liquid phase, preferably in liquid phase. In fact the liquid phase reaction makes it possible to reduce the energy costs and to increase the cycle duration of the catalyst. For a liquid phase reaction the pressure is generally between 1 and 3 MPa, the temperature is between 2 and 50° C. and the molar ratio (hydrogen)/(polyunsaturated compounds to be hydrogenated) is between 0.1 and 4, preferably between 1 and 2. The HSV is between 10 $h^{-1}$ and 50 $h^{-1}$.

For a gaseous phase hydrogenation reaction the pressure is generally between 1 and 3 MPa, the temperature is between 40 and 120° C. and the molar ratio (hydrogen)/(polyunsaturated compounds to be hydrogenated) is between 0.1 and 4, preferably between 1 and 2 and the HSV (charge flow rate per volume of catalyst) is between 500 $h^{-1}$ and 5000 $h^{-1}$.

In the case of selective hydrogenation of dripolene the molar ratio (hydrogen)/(polyunsaturated compounds to be hydrogenated) is generally between 1 and 2, the temperature is generally between 40° C. and 200° C., preferably between 50 and 180° C., the HSV is generally between 0.5 $h^{-1}$ and 10 $h^{-1}$, preferably between $1^{-1}$ and 5 $h^{-1}$ and the pressure is generally between 1.0 MPa and 6.5 MPa, preferably between 2.0 MPa and 3.5 MPa. The hydrogen flow rate is adjusted in order to have a sufficient amount thereof for theoretically hydrogenating all of the polyunsaturated compounds and maintaining an excess of hydrogen at the reactor outlet. To limit the temperature gradient in the reactor it may be advantageous to recycle a fraction of the effluent to the intake and/or to the middle of the reactor. The dripolene corresponds to a cut of which the boiling temperature is generally between 0° C. and 250° C., preferably between 10° C. and 220° C. That charge generally comprises the C5-C12 cut with traces of C3, C4, C13, C14, C15 compounds (for example between 0.1 and 3% by weight for each of the those cuts). For example a charge formed by dripolene is generally of a composition in % by weight as follows: 8 to 12% by weight of paraffins, 58 to 62% by weight of aromatic compounds, 8 to 10% by weight of monoolefins, 18 to 22% by weight of diolefins and 20 to 300 ppm by weight of sulphur (part per million), the total of the compounds forming 100%.

The invention is illustrated by the following Examples which do not in any case with involve a limiting character.

EXAMPLES

Example 1

Catalyst A (Not According to the Invention)

An aqueous solution of palladium nitrate $Pd(NO_3)_2$ is prepared by the dilution of 10.88 g of an aqueous solution of palladium nitrate $Pd(NO_3)_2$ containing 10% by weight of palladium nitrate and 10% by weight of nitric acid (Aldrich) with demineralised water to a volume corresponding to the porous volume of the support. The pH of that solution is 0.74. No palladium oxide particle is distinguished by transmission electron microscopy.

That solution is then impregnated on 100 g of an alumina whose specific surface area is 140 m$^2$/g and which involves a porous volume of 1.02 ml/g. That alumina is in the form of balls of a mean diameter of 3 mm.

The resulting catalyst A is dried in air at 120° C. and then calcined for 2 hours at 450° C. in a flow of air at an HSV of 500 h$^{-1}$. The catalyst A contains 0.5% by weight of Pd with respect to the weight of the support.

Example 2

Catalyst B (Not According to the Invention)

A solution containing 0.57 g of sodium hydroxide (Prolabo) in 15 ml of demineralised water is inserted into 10.88 g of an aqueous solution of palladium nitrate $Pd(NO_3)_2$ containing 10% by weight of palladium nitrate and 10% by weight of nitric acid (Aldrich). That solution is then diluted with demineralised water to a volume corresponding to the porous volume of the support. The pH of that solution is 1.4. Transmission electron microscopy is used to distinguish agglomerates of 20 to 100 nm of palladium oxide nanoparticles of 1 to 3 nm in diameter and palladium oxide nanoparticles which are isolated from each other of 1 to 3 nm in diameter. Less than 10% of the particles are in the form of agglomerates.

That solution is then impregnated on 100 g of an alumina whose specific surface area is 140 m$^2$/g and which involves a porous volume of 1.02 ml/g. That alumina is in the form of balls whose mean diameter is 3 mm.

The resulting catalyst B is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst B contains 0.5% by weight of Pd with respect to the weight of the support.

Example 3

Catalyst C 0.31 g of an aqueous solution containing 40% by weight of tetrabutylammonium hydroxide (TBAOH, Aldrich) is added with agitation to 10.88 g of an aqueous solution of palladium nitrate $Pd(NO_3)_2$ containing 10% by weight of palladium nitrate and 10% by weight of nitric acid (Aldrich). That solution is diluted with demineralised water to a volume which corresponds to the porous volume of the support, in which 1.11 g of sodium hydroxide (Prolabo) has been previously dissolved. The TBAOH/Pd molar ratio in the impregnation solution is equal to 0.1. The pH of the solution is 11.2. Transmission electron microscopy is used to distinguish agglomerates of 20 to 100 nm of palladium oxide nanoparticles of 1 to 3 nm in diameter and palladium oxide nanoparticles which are isolated from each other of 1 to 3 nm in diameter. More than 60% of the particles are in the form of agglomerates.

That solution is then impregnated on 100 g of an alumina whose specific surface area is 140 m$^2$/g and which is of a porous volume of 1.02 ml/g. That alumina is in the form of balls whose mean diameter is 3 mm.

The resulting catalyst C is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst C contains 0.5% by weight of Pd with respect to the weight of the support.

Example 4

Catalyst D 10.88 g of an aqueous solution of palladium nitrate $Pd(NO_3)_2$ containing 10% by weight of palladium nitrate and 10% by weight of nitric acid (Aldrich) is added with agitation to 18.29 g of an aqueous solution comprising 40% by weight of tetrabutylammonium hydroxide (TBAOH, Aldrich). That solution is diluted with demineralised water to a volume which corresponds to the porous volume of the support. The TBAOH/Pd molar ratio in the impregnation solution is equal to 6. The pH of the solution is 8.2. Transmission electron microscopy is used to distinguish agglomerates of 20 to 100 nm of palladium oxide nanoparticles of 2 to 3 nm in diameter and palladium oxide nanoparticles which are isolated from each other of 1 to 3 nm in diameter. More than 90% of the particles are in the form of agglomerates.

That solution is then impregnated on 100 g of an alumina whose specific surface area is 140 m$^2$/g and which is of a porous volume of 1.02 ml/g. That alumina is in the form of balls whose mean diameter is 3 mm.

The resulting catalyst D is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst D contains 0.5% by weight of Pd with respect to the weight of the support.

Example 5

Catalyst E 2.18 g of an aqueous solution of palladium nitrate $Pd(NO_3)_2$ containing 10% by weight of palladium nitrate and 10% by weight of nitric acid (Aldrich) is added with agitation to 3.66 g of an aqueous solution comprising 40% by weight of tetrabutylammonium hydroxide (TBAOH, Aldrich). That solution is diluted with demineralised water to a volume which corresponds to the porous volume of the support. The TBAOH/Pd molar ratio in the impregnation solution is equal to 6. The pH of the solution is 10.1. Transmission electron microscopy is used to distinguish agglomerates of 20 to 100 nm of palladium oxide nanoparticles of 2 to 3 nm in diameter and palladium oxide nanoparticles which are isolated from each other of 1 to 3 nm in diameter. More than 80% of the particles are in the form of agglomerates.

That solution is then impregnated on 100 g of an alumina whose specific surface area is 140 m$^2$/g and which is of a porous volume of 1.02 ml/g. That alumina is in the form of balls whose mean diameter is 3 mm.

The resulting catalyst E is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst E contains 0.1% by weight of Pd with respect to the weight of the support.

Example 6

Catalyst F 10.88 g of an aqueous solution of palladium nitrate Pd(NO$_3$)$_2$ containing 10% by weight of palladium nitrate and 10% by weight of nitric acid (Aldrich) is added with agitation to 20.76 g of an aqueous solution comprising 20% by weight of tetraethylammonium hydroxide (TEAOH, Aldrich). That solution is diluted with demineralised water to a volume which corresponds to the porous volume of the support. The TEAOH/Pd molar ratio in the impregnation solution is equal to 6. The pH of the solution is 10.6. Transmission electron microscopy is used to distinguish agglomerates of 20 to 100 nm of palladium oxide nanoparticles of 2 to 3 nm in diameter and palladium oxide nanoparticles which are isolated from each other of 1 to 3 nm in diameter. More than 90% of the particles are in the form of agglomerates.

That solution is then impregnated on 100 g of an alumina whose specific surface area is 140 m$^2$/g and which is of a porous volume of 1.02 ml/g. That alumina is in the form of balls whose mean diameter is 3 mm.

The resulting catalyst F is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst F contains 0.5% by weight of Pd with respect to the weight of the support.

Example 7

Catalyst G

A solution containing 0.81 g of sodium hydroxide (Prolabo) and 0.68 g of sodium dodecyl sulphate (DS, Aldrich) in 15 ml of demineralised water is inserted into 10.88 g of an aqueous solution of palladium nitrate Pd(NO$_3$)$_2$ containing 10% by weight of palladium nitrate and 10% by weight of nitric acid (Aldrich). That solution is then diluted with demineralised water to a volume corresponding to the porous volume of the support. The DS/Pd molar ratio in the impregnation solution is equal to 0.5. The pH of that solution is 1.71. Transmission electron microscopy is used to distinguish agglomerates of 20 to 100 nm of palladium oxide nanoparticles of 1 to 3 nm in diameter and palladium oxide nanoparticles which are isolated from each other of 1 to 3 nm in diameter. More than 70% of the particles are in the form of agglomerates.

That solution is then impregnated on 100 g of an alumina whose specific surface area is 140 m$^2$/g and which involves a porous volume of 1.02 ml/g. That alumina is in the form of balls whose mean diameter is 3 mm.

The resulting catalyst G is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst G contains 0.5% by weight of Pd with respect to the weight of the support.

Example 8

Catalyst H

A solution containing 0.81 g of sodium hydroxide (Prolabo) and 0.82 g of sodium dodecylbenzene sulphonate (DBS, Aldrich) in 15 ml of demineralised water is inserted into 10.88 g of an aqueous solution of palladium nitrate Pd(NO$_3$)$_2$ containing 10% by weight of palladium nitrate and 10% by weight of nitric acid (Aldrich). That solution is then diluted with demineralised water to a volume corresponding to the porous volume of the support. The DBS/Pd molar ratio in the impregnation solution is equal to 0.5. The pH of that solution is 1.74. Transmission electron microscopy is used to distinguish agglomerates of 20 to 100 nm of palladium oxide nanoparticles of 1 to 3 nm in diameter and palladium oxide nanoparticles which are isolated from each other of 1 to 3 nm in diameter. More than 70% of the particles are in the form of agglomerates.

That solution is then impregnated on 100 g of an alumina whose specific surface area is 140 m$^2$/g and which involves a porous volume of 1.02 ml/g. That alumina is in the form of balls whose mean diameter is 3 mm.

The resulting catalyst H is dried in air at 120° C., then calcined for 2 hours at 150° C., then 2 hours at 200° C., then 2 hours at 300° C., then 2 hours at 450° C. in a flow of a mixture comprising 25% by volume of air and 75% by volume of nitrogen at an HSV of 2000 h$^{-1}$. The catalyst H contains 0.5% by weight of Pd with respect to the weight of the support.

Example 9

Catalytic Test in Respect of Hydrogenation of a Styrene Isoprene Mixture

Before the catalytic test the catalysts A, B, C, D, E, F, G and H are treated in a flow of hydrogen at an HSV of 500 h$^{-1}$ with a rise in temperature of 300° C./h and a hold at a final temperature of 150° C. for 2 hours.

The catalysts are then subjected to a hydrogenation test in a perfectly agitated discontinuous reactor of "Grignard" type. To do that 4 ml of reduced catalyst balls are fixed sheltered from air in an annular basket disposed around the movable agitation member. The baskets used in the reactors are of Robinson Mahonnay type.

Hydrogenation is effected in the liquid phase.

The composition of the charge is as follows: 8% by weight of styrene, 8% by weight of isoprene and 74% by weight of n-heptane.

The test is carried out under a constant pressure of 3.5 MPa of hydrogen and at a temperature of 45° C.

The products of the reaction are analysed by gas phase chromatography.

The catalytic activities are expressed in mols of H$_2$ consumed per minute and per gram of palladium and are set forth in Table 1.

TABLE 1

Measured activities in respect of hydrogenation of a styrene isoprene mixture

| Catalyst | Activity* |
| --- | --- |
| Catalyst A (not according to the invention | 1.84 |
| Catalyst B (not according to the invention) | 2.73 |
| Catalyst C | 4.29 |
| Catalyst D | 6.43 |
| Catalyst E | 10.70 |
| Catalyst F | 6.82 |
| Catalyst G | 6.38 |
| Catalyst H | 5.89 |

*in (mols $H_2$)/[min × (gram of palladium)]

The catalysts C, D, E, F, G and H according to the invention are about 1.5 to 6 times more active than the catalysts A and B not according to the invention.

Example 10

Distribution of the Metallic Phase on the Support

To analyse the distribution of the metallic phase on the support a crust thickness is measured by Castaing microprobe (or electron probe microanalyser). The apparatus used is a CAMECA XS100 equipped with four monochromator crystals permitting simultaneous analysis of four elements. The Castaing microprobe analysis procedure involves detection of X-rays emitted by a solid after excitation of its elements by a high-energy electron beam. For the purposes of this characterisation the catalyst balls are encased in epoxy resin blocks. They are polished until reaching the cut at the diameter of the balls, then metallised by deposit of carbon in a metallic evaporator. The electron probe is swept along the diameter of five balls to produce the mean distribution profile of the elements constituting the solids.

To measure a crust thickness which is significant for the majority of the palladium particles the crust thickness can alternatively be defined as the distance to the edge of the grain containing 80% by weight of palladium. On the basis of the distribution profile obtained by the Castaing microprobe ("c(x)") it is possible to calculate the cumulated amount of Pd in the grain in dependence on the distance "y" to the edge of the grain of a radius "r". For a ball:

$$Q(y) = \int_{-r}^{-y} c(x) \cdot 4 \cdot \pi \cdot x^2 \cdot dx + \int_{y}^{r} c(x) \cdot 4 \cdot \pi \cdot x^2 \cdot dx$$

Q(r) thus corresponding to the total amount of Pd in the grain. The following equation in respect of y is then numerically resolved to obtain the crust thickness at 80% by weight of palladium:

$$\frac{Q(y)}{Q(r)} = 0.8$$

The crust thicknesses of the different catalysts are set forth in Table 2.

TABLE 2

Metallic crust thicknesses measured by Castaing microprobe.

| Catalyst | Crust thickness (in μm) comprising 80% by weight of Pd * |
| --- | --- |
| Catalyst A (not according to the invention | 125 |
| Catalyst B (not according to the invention) | 73 |
| Catalyst C | 54 |
| Catalyst D | 36 |
| Catalyst E | 21 |
| Catalyst F | 35 |
| Catalyst G | 38 |
| Catalyst H | 43 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosures of all applications, patents and publications, cited herein and of corresponding French application No. 10/04.878, filed Dec. 14, 2010, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a catalyst comprising the following steps:
   (a) preparing a colloidal aqueous suspension of nanoparticles of metallic oxide, whereby at least 20% by number of the nanoparticles are in the form of agglomerates of a size of 10-200 nm,
   (b) depositing said agglomerates obtained in step (a) on a porous support, and
   (c) drying the product obtained in step (b).

2. The preparation process according to claim 1 further comprising after step (c) at least a step (d) for calcination of the product obtained in step (c).

3. The preparation process according to claim 1 further comprising and after one of steps (c) or (d) at least a step for reduction of the product obtained in step (c) or (d).

4. The process according to claim 1, wherein at least 50% of the nanoparticles are in the form of agglomerates of a size of 10-200 nm.

5. The process according to claim 1, wherein at least 50% of the nanoparticles are in the form of agglomerates of a size of 20-95 nm.

6. The preparation process according to claim 1 wherein the colloidal aqueous suspension is obtained by hydrolysis in aqueous solution of at least one salt of a metallic precursor and in the presence of at least one agglomerating agent.

7. The preparation process according to claim 6 wherein the metal of said metallic precursor salt is a metal of group VIII.

8. The preparation process according to claim 6 in which said salt of a metallic precursor is a halide, an oxide, a hydroxide, a nitrate or a sulphate of the metal.

9. The preparation process according to claim 6 wherein the molar ratio between the agglomerating agent and the salt of a metallic precursor is between 0.001 and 100.

10. The preparation process according to claim 6 wherein when the pH of the colloidal aqueous solution is higher than the zero charge point of the metal oxide, the agglomerating agent is a cationic agglomerating agent of the formula $(R)_n$—X wherein:
- X a cation,
- n is equal to 4, and
- R is identical or different and is a straight-chain or branched-chain alkyl comprising 2 to 5 carbon atoms.

11. The preparation process according to claim 6 wherein when the pH of the colloidal solution is lower than the zero charge point of the metal oxide, the agglomerating agent is an anionic agglomerating agent of the formula $(R)_n$—X wherein:
- X is an anion,
- n is equal to 1, and
- R is a group of the formula $(B)_p$-$(A)_m$→ wherein
  m is an integer equal to 0 or 1,
  p is an integer equal to 0 or 1,
  A is a substituted or unsubstituted aromatic,
  B is a straight-chain or branched-chain hydrocarbon chain comprising between 5 and 14 carbon atoms,
  → symbolises attachment of the group R to X by a covalent bond.

12. The preparation process according to claim 6 wherein the hydrolysis operation is effected by neutralization with at least one inorganic acid.

13. A catalyst obtained by the process according to claim 1.

14. A process for the transformation of organic compounds, comprising subjecting said compounds to a catalyst of claim 13.

15. The process according to claim 14 wherein the reaction is a reaction for cuts or formations of a carbon-carbon bond.

16. The process according to claim 14 wherein the reaction is a reaction for the selective hydrogenation of compounds comprising at least one function selected from the group formed by the acetylenic, dienic, olefinic, aromatic, aldehyde, acid and nitro functions.

17. The process according to claim 14 wherein the reaction is a reaction for the selective hydrogenation of compounds comprising at least one dienic and/or acetylenic function.

18. A process for the preparation for a palladium and/or nickel catalyst comprising the following steps:
- a) preparing a colloidal aqueous suspension of nanoparticles of metallic oxide, said preparation consists of an hydrolysis in aqueous solution of at least one salt of a metallic precursor and in the presence of at least one agglomerating agent, said metal of said metallic precursor salt being selected from palladium and/or nickel, said salt of
- b) said metallic precursor is selected from the group formed by a halide, a nitrate and a sulphate, the colloidal suspension obtained is such that between 20% and 95% by number of the nanoparticles of metal oxide are formed of agglomerates and the size for the agglomerates is between 20 and 200 nm,
- c) depositing said agglomerates obtained in step (a) on a porous support, and
- d) drying the product obtained in step (b).

* * * * *